US009321794B2

(12) United States Patent
Meckler et al.

(10) Patent No.: US 9,321,794 B2
(45) Date of Patent: Apr. 26, 2016

(54) SYNTHESIS OF RACEMIC AMPHETAMINE DERIVATIVES BY CUPRATE ADDITION REACTION WITH AZIRIDINE PHOSPHORAMIDATE COMPOUNDS

(71) Applicant: Chemapotheca, LLC, Delmar, NY (US)

(72) Inventors: Harold Meckler, Delmar, NY (US); Brian Thomas Gregg, Altamont, NY (US); Jie Yang, Rensselaer, NY (US)

(73) Assignee: CHEMAPOTHECA, LLC, Delmar, NY (US)

( * ) Notice: Subject to any disclaimer, the term of this patent is extended or adjusted under 35 U.S.C. 154(b) by 0 days.

(21) Appl. No.: 14/327,209

(22) Filed: Jul. 9, 2014

(65) Prior Publication Data

US 2015/0183810 A1 Jul. 2, 2015

Related U.S. Application Data

(63) Continuation-in-part of application No. 14/189,630, filed on Feb. 25, 2014.

(60) Provisional application No. 61/922,729, filed on Dec. 31, 2013.

(51) Int. Cl.
| | | |
|---|---|---|
| C07F 9/22 | (2006.01) | |
| C07F 9/564 | (2006.01) | |
| C07F 9/02 | (2006.01) | |
| C07C 209/62 | (2006.01) | |
| C07F 9/24 | (2006.01) | |

(52) U.S. Cl.
CPC .............. C07F 9/564 (2013.01); C07C 209/62 (2013.01); C07F 9/2458 (2013.01); C07F 9/2475 (2013.01)

(58) Field of Classification Search
None
See application file for complete search history.

(56) References Cited

U.S. PATENT DOCUMENTS

| 6,399,828 B1 | 6/2002 | Boswell |
| 7,705,184 B2 | 4/2010 | Buenger |
| 8,487,134 B2 | 7/2013 | Meudt |

FOREIGN PATENT DOCUMENTS

FR                  5.857 M          3/1968

OTHER PUBLICATIONS

L.A. Cates, et al., "Phosphorus-Nitrogen Compounds VI: Some Phenethylamine Derivatives," *Journal of Pharmaceutical Sciences*, vol. 55, No. 12, Dec. 1996, pp. 1400-1405.
P. Giles, et al. "An Improved Process for the N-Alkylation of Indoles Using Chiral N-Protected 2-Methylaziridines," *Organic Process Research & Development*, vol. 7, No. 1, 2003, pp. 22-24.
A. Poshkus, et al., "The Reaction of Neutral Esters of Trivalent Phosphorus Acids with Inorganic Acid Chlorides. I. The Reaction of Trialkyl Phosphites with Sulfuryl Chloride," *Journal of the American Chemical Society*, Contribution from the Research and Development Center of the Armstrong Cork Co., 1957, pp. 6127-6129.
A. Bořkovec, et al., Insect Chemosterilants. III. 1-Aziridinylphosphine Oxides, *Journal of Medicinal Chemistry*, vol. 9, Jul. 1966, pp. 522-526.
N. Stojanovska, et al., "A Review of Impurity Profiling and Synthetic Route of Manufacture of Methylamphetamine, 3,4-methylenedioxymethylamphetamine, amphetamine, dimethylamphetamine and p-methoxyamphetamine," *Forensic Science International*, vol. 224, 2013, pp. 8-26.
Koziara, A.; Oleiniczak, B.; Osowska, K.; Zwierzak, A. "Phosphoramidomercuration-Demercuration: A Simple Two-Step Conversion of Alkenes into Alkanamines" *Synthesis* 1982, 918-920.
Stephans, W. D.; Moffett, L. R.; Vaughan, H. W.; Hill, W. E.; Brown, S. P. "Substituted Aziridines: Preparation and Properties" *Journal of Chemical and Engineering Data* 1963, 8, 625-626.
Stephans, W. D.; Moffett, L. R.; Vaughan, H. W.; Taylor, C. O.; Brown, S. P.; Ashmore, C. I. Substituted Aziridines: Relative Rates of Reaction and Direction of Ring Opening *Journal of Chemical and Engineering Data* 1969, 14, 114-116.
Hassner, A.; Galle, J. E.; "Ring Opening of Aziridine Phosphonates. Correlation of Structure, Nuclear Magnetic Resonance Spectra and Reactivity" *J. Org. Chem.*, 1976, 41, 2273-2276.
Zwierzak, A,; Brylikowska-Piotrowicz, J.; "Alkylation of Diethyl Phosphoramidates—A Simple Route from Primary Amines to Secondary Amines" *Angew. Chem. Int. Ed. Engl.* 1977, 16, 107.
Jagmin, Jeff; "What's in Your NWAFS Spring", Crime Scene, vol. 37, Issue 2, Spring 2011, p. 1-52.
WO 2015/130660 Int'l Search Report, Jun. 25, 2015, Chemapotheca.
WO 2015/130661 Int'l Written Opinion of '661 ISR, Jun. 25, 2015, Chemapotheca.
WO 2015/130661 Int'l Search report, Jun. 25, 2015, Chemapotheca.
WO 2015/130661 Int'l Written Opinion of '661 ISR, Jun. 29, 2015, Chemapotheca.
Kojima, Scifinder CAS Registry 1485-13-8 for 2-methyl-3-phenyl-aziridine, Kojima 1959 et al., (Scifinder printout only).

(Continued)

*Primary Examiner* — Rebecca Anderson
*Assistant Examiner* — Po-Chih Chen
(74) *Attorney, Agent, or Firm* — Juneau & Mitchell; Todd L. Juneau

(57) ABSTRACT

The invention includes processes for the synthesis of amphetamine, dexamphetamine, methamphetamine, derivatives of these, including their salts, and novel precursors and intermediates obtained thereby, by synthesizing aziridine phosphoramidate compounds in specified solvents at specified temperatures, and then converting to a novel aryl or aryl-alkyl phosphoramidate precursors using an organometallic compound such as a copper salt, where the novel aryl or aryl-alkyl phosphoramidate precursor is then easily converted to the target compounds using known reactions.

29 Claims, No Drawings

(56) References Cited

OTHER PUBLICATIONS

Streuff—Aziridines—Overview and Recent Advancements, Stoltzgroup Literature Seminar, Jan. 26, 2009.
Mekenyan, Scifinder 2010:1165579 ACS, Aziridine Use of Genotoxicity Information . . . , Chem Res Tox vol. 23 Issue 10 pp. 1519-1540, 2010, (Scifinder printout only).
Sakurai, Scifinder 2000-630740 ACS, Aziridine Recommendation of Occupational exposure limits, J Occup Health, vol. 42, Issue 4, pp. 213-228, 2000 (Scifinder printout only).
Koleva, Scifinder 2011-1058228 ACS, Modelling of Acute Oral . . . aziricline toxicity, Toxicology InVitro, vol. 25, Issue 7, pp. 1281-1293, 2011, (Scifinder printout only).
Lambrechts, Leuckart-specific impurities in amphetamine, Bulletin on Narcotics, UNODC Everywhere, pp. 47-57, Jan. 1, 1984.
D'Ambra, Scifinder Search Results for D'Ambra patents (allergy drugs, regioselectivity) Accession 2002-52000, from U520020007068, 1999, (Scifinder printout only).
Rege et al. Drug Metabolism and Disposition, vol. 30 No. 12, pp. 1337-1343, Irreversible Inhibition of CYP2D6 by (-) Chloroephedrine (impurity), 2002.
EMEA Committee for Medical Products, Grignard Solvents Committee, Feb 10, 2005, pp. 1-7.
FDA CDER Guidance for Industry, (genotox guidance) Dec. 2008.
Skinner, Methamphetamine Synthesis via Hydriodic . . . , Forensic Sci Int'l, 48 (1990) 123-134, red phos method, 1990.
Anderson, Development of a Harmonized Method for Profiling . . . , Forensic Sci Int'l 169 (2007) pp. 50-63, GC method.
Power, An Unusual Presentation of Customs Seizure, Forensic Sci Int'l 234 (2014) e10-e13, 2014.
Barker, A Study of the Use of Ephedra, Forensic Sci Int'l 166 (2007) 102-109.
Humphrey, Keeping Afloat in a Sea of Impurities, Global Safety Assessment, Astra Zeneca Jul. 6, 2007.
EMEA Solvent (Grignard) impurities, ICH Topic Q3C (R4), pp. 1-22, 2010.
Funel and Abele, Diels Alder Reactions Part 1, Angewandte Reviews, Angew. Chem Int 2013 vol. 52, 1-44, 2013.
Funel and Abele, Diels Alder Reactions Part 3, Angewandte Reviews, Angew. Chem Int 2013 vol. 52, 1-44, 2013.
Funel and Abele, Diels Alder Reactions Part 2, Angewandte Reviews, Angew. Chem Int 2013 vol. 52, 1-44, 2013.
Funel and Abele, Diels Alder Reactions Part 4, Angewandte Reviews, Angew. Chem Int 2013 vol. 52, 1-44, 2013.
Stephens, Substituted Aziridines, Prep and Properties, J Chem Engin, vol. 8, No. 4, pp. 625-626, Oct. 1963.
Stephens, Relative rates of Reaction and Direction of Ring Opening, J Chem Engin, vol. 14, No. 1, pp. 114-115, Jan. 1969.
HATA, Fragmentation Reaction of Ylide, JACS vol. 98-19, pp. 6033-6036, Sep. 1976.
Jessing, Aziridines in Synthesis, Baran Lab Jan. 2007.
Stromberg, Comparative GC Analysis, J Chromatography 106 (1975) 335-342, amphet sulfate.
Power, An Unusual Presentation of Customs Seizure, Forensic Sci Int'l 234 (2014) e10-e13.
Allen, Methamphetamines from Ephedrine, J Forensic Sci vol. 32, No. 4, Jul. 1987, pp. 953-962.
Milstein, Friedel Crafts Reactions of Htree Member Heterocycles, J Het Chem vol. 5, pp. 339-241, Mar. 1968.
Hassner, Regiospecificity: A Useful Terminology, JOC vol. 33, No. 7 pp. 2684-2686 Jul. 1968.
Todd, Aneurin, A Synthesis of Thiochrome, J Chem Soc 1936, pp. 1601-1605.
Hider, Prep of Evidence in Amphet Prosecutions, J Forensic Sci pp. 75-79 1960's, 1960.
Anandasankar , Scifinder 7763-71-5, referring to WO 2011 130726, priority to US 2011-32804, and 2010-61325236, 2010, (Scifinder printout only).
Osowska-Pacewicka, N-Phosphorylated Aziridines—new reagents for electrophilic amination, Polish J Chem 68-6 pp. 1263-64 1994, (Scifinder printout only).
Pramanik, An Efficient Scalable Process for Benzphetamine HCl, JACS J Org Process Res Dev 2014 vol. 18 pp. 495-500, 2014.
Snodin, Potentially Mutagenic Impurities, J Org Process Res Dev 2014, vol. 18, pp. 836-839 Racemic.
Raman, Regulatory Expectations Towards Genotoxic, J Org Process Res Dev 2014 vol. 18 pp. 834-835.
Teasdale, Regulatory Highlights, J Org Process Res Dev 2014 vol. 18, 458-472.
Jawahar, Direct Stereospecific Synthesis of Unprotected N-H and N-Me Aziridines from Olefins, Sciences 343, 61 pp. 61-65, 2014.

SYNTHESIS OF RACEMIC AMPHETAMINE DERIVATIVES BY CUPRATE ADDITION REACTION WITH AZIRIDINE PHOSPHORAMIDATE COMPOUNDS

CROSS-REFERENCE TO RELATED APPLICATIONS

This application is a continuation-in-part of U.S. application Ser. No. 14/189,630 filed Feb. 25, 2014, the content of which is incorporated herein in its entirety.

STATEMENT REGARDING FEDERALLY SPONSORED RESEARCH

No federal government funds were used in the research or development of this invention.

NAMES OF PARTIES TO A JOINT RESEARCH AGREEMENT

None.

REFERENCE TO A SEQUENCE LISTING

None.

BACKGROUND

1. Field of the Invention

This is invention is related to processes for synthesis of amphetamine derivatives and novel intermediates thereby.

2. Background of the Invention

The commercial importance of amphetamine derivatives has led to the development of numerous synthetic methods for their synthesis and their derivatization. One problem with amphetamine synthesis is that amphetamines have a stereo-defined amine center, which can be difficult to resolve and subject to racemization. Accordingly, for the preparation of a single stereoisomer, only stereospecific methods are useful. However, stereospecific methods do not provide the economic requirements of high yields, high selectivity and low process costs. Typically, the stereo center is purchased as part of a chiral starting material or utilize tedious and expensive synthetic reactions to achieve that goal. Such reactions involve a coupling agent, such as Grignard or organolithium reagents. Conventional teaching requires that the use such organometallics requires that the reaction temperature be maintained at a cold temperature, such as an ice bath at less than 10 degrees Celsius.

To complicate the amphetamine marketplace, there are established formulations which require racemic amphetamine to obtain an extended release of elevated blood levels of the drug. This racemic material can be obtained by mixing equal parts of the dextrorotary and levorotary stereos isomers or running a synthetic sequence which only produces racemic amphetamine.

Another problem with amphetamine synthesis is that the intermediates are toxic as well as flammable. This requires special handling such as double-walled drums and safety accommodations to protect manufacturing personnel.

The prior art in U.S. Pat. No. 6,399,828 teaches the production of amphetamine using various methods. In one approach norephedrine is refluxed with hydrogen iodide and red phosphorous. In another approach norephedrine is chlorinated using thionyl chloride and then catalytically hydrogenated. In U.S. Pat. No. 7,705,184, amphetamine synthesis is disclosed using hydrogenation of a chlorinated phenylpropanolamine. Aziridine chemistry, and specifically aziridine phosphoramidates are not taught in the amphetamine synthesis prior art.

Zwierzak et al. disclose a method of reacting N-phosphorylated aziridines with copper-modified Grignard reagents as a new route to substituted pyrrolines and pyrrolidines. However, Zwierzak et al discloses this method as being regiospecific, which it is not. Synthetic Communications: An Int'l J. for Rapid Commun. of Syn. Org. Chem., 28:7, 1127-1137 (1998).

Additionally, the use of protecting groups and leaving groups is well known. However, it has been discovered that there is significant variation among the various standard protecting groups. Specifically, where a carbonyl moiety is used as the amine protecting group (i.e. acetyl t-Boc or CBZ), the reaction must be kept at or below −10 degrees Celsius or the carbonyl will react with the organometallic reagent. Where a sulfonyl moiety is used as an amine protecting group (i.e. methanesulfonyl or p-toluenesulfonyl), it is difficult to remove the protecting group without destroying the molecule.

Accordingly, there is a need for synthetic processes and useful compounds for the manufacture of amphetamine and its derivatives that have high chemical yield, high selectivity, low cost, lower toxicity and are less dangerous to handle.

BRIEF SUMMARY OF THE INVENTION

The present invention addresses one or more of the shortcomings of the prior art by providing processes for the synthesis of amphetamine, dexamphetamine, methamphetamine, derivatives of these, including their salts, and novel precursors and intermediates obtained thereby, by synthesizing aziridine phosphoramidate compounds in specified solvents at specified temperatures, and then converting to a novel aryl or aryl-alkyl phosphoramidate precursors using a modified organometallic compound such as a organocopper reagent, where the novel aryl or aryl-alkyl phosphoramidate precursor is then easily converted to the target compounds using known reactions, e.g. acidification, alkylation of the nitrogen followed by dephosphorylation, etc.

In one preferred aspect the invention provides a synthetic pathway to amphetamine derivatives using an aziridine based process with an organometallic compound by heating the reactants in a first step, and then adding as a second step the Grignard reagent in a dosage controlled fashion. In a preferred embodiment, the reaction is heated to above 40 degrees C., preferably above about 45 degrees C., and more preferably above about 48 degrees C. In one embodiment, the temperature is maintained from 48-51 deg. C. for about 30 minutes and then brought to room temperature.

In another preferred embodiment, the invention provides a process of making the amphetamine, said process comprising:

providing a compound of Formula 6:

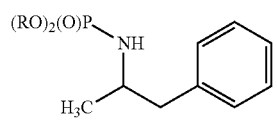

wherein R is alkyl or aryl; and deprotecting the compound of Formula 6 under acidic conditions effective to produce amphetamine of Formula 7:

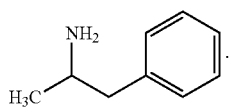

In preferred aspects, the amphetamine process comprises wherein the acidic conditions are aqueous hydrochloric, sulfuric or phosphoric acids.

In preferred aspects, the amphetamine process comprises wherein the aqueous acid water content is in an amount of 50% to 90%

In preferred aspects, the amphetamine process comprises wherein the R=methyl, ethyl, isopropyl or phenyl.

In preferred aspects, the amphetamine process comprises wherein said providing a compound of Formula 6 comprises:
providing a compound of Formula 2:

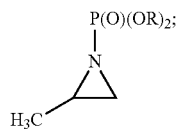

wherein R is alkyl or aryl and
reacting the compound of Formula 2 with phenylmagnesium halide and a copper catalyst under solvent and temperature conditions effective to produce a compound of Formula 6 in a purity substantially free of any regioisomeric impurities.

In preferred aspects, the amphetamine process comprises wherein the regioisomeric purity of Formula 6 is >99% and the regioisomer (Formula 8) is <0.1%.

In preferred aspects, the amphetamine process comprises wherein the R=methyl, ethyl, isopropyl or phenyl.

In preferred aspects, the amphetamine process comprises wherein the copper catalyst is $CuCl$, $CuCl_2$, $CuBr$, $CuF$, $CuI$, $Cu(OAc)_2$, $Cu(OMe)2$, Copper nanoparticles, Copper turnings, or combinations thereof.

In preferred aspects, the amphetamine process comprises wherein the solvent is an organic ether or an organic ether-toluene mixture.

In preferred aspects, the amphetamine process comprises wherein the organic ether solvent is diethyl ether, tetrahydrofuran or 2-methyltetrahydrofuran.

In preferred aspects, the amphetamine process comprises wherein the phenylmagnesium halide is either phenylmagnesium chloride, phenylmagnesium bromide or phenylmagnesium iodide.

In preferred aspects, the amphetamine process comprises wherein the phenylmagnesium halide solutions can either be commercially supplied or prepared in situ from the corresponding halobenzene and magnesium.

In preferred aspects, the amphetamine process comprises wherein the magnesium is be in the form of chips, granules, ribbon, turnings, dust, grit, blocks or chunks.

In preferred aspects, the amphetamine process comprises wherein said treating is carried out at a temperature of from about −10° C. to about 70° C.

In preferred aspects, the amphetamine process comprises wherein said treating is carried out at a temperature of from about 30° C. to about 60° C.

In preferred aspects, the amphetamine process comprises wherein said providing a compound of Formula 2 comprises:
providing a compound of Formula 5:

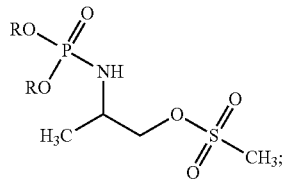

wherein R is alkyl or aryl; and
reacting the compound of Formula 5 with the base under conditions effective to produce a compound of Formula 2.

In preferred aspects, the amphetamine process comprises a compound of Formula 5 wherein the R=methyl, ethyl, isopropyl or phenyl.

In preferred aspects, the amphetamine process comprises wherein the base is potassium hydroxide or potassium carbonate.

In preferred aspects, the amphetamine process comprises wherein said providing a compound of Formula 5 comprises:
providing a compound of Formula 4:

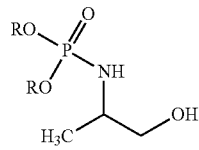

wherein R is alkyl or aryl; and
reacting the compound of Formula 4 with methanesulfonyl chloride and a base under conditions effective to produce a compound of Formula 5.

In preferred aspects, the amphetamine process comprises a compound of Formula 4 wherein the R=methyl, ethyl, isopropyl or phenyl.

In preferred aspects, the amphetamine process comprises wherein said providing a compound of Formula 4 comprises:
providing a compound of Formula 3:

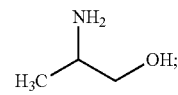

and
reacting the compound of Formula 3 with the appropriate

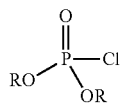

wherein R=alkyl or aryl
under conditions effective to produce a compound of Formula 4.

In preferred aspects, the amphetamine process involving Formula 4 comprises wherein the R=methyl, ethyl, isopropyl or phenyl.

In another preferred embodiment, the invention provides a compound of formula 6:

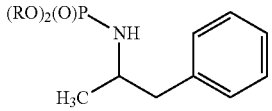
6 prepared according to one or more processes herein, in a regioisomeric purity of >1700:1
wherein:
R is alkyl or aryl
In preferred aspects, the invention further comprises a compound of formula 6:

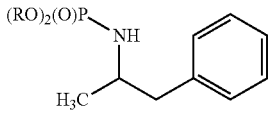
6 wherein the alkyl group is selected from the group consisting of methyl, ethyl or isopropyl.
In preferred aspects, the invention further comprises a compound of formula 6:

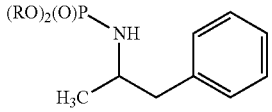
6 wherein the aryl group is phenyl.
In another preferred embodiment, the invention provides a compound of formula 2:

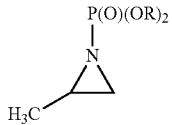
2 wherein: R is alkyl or aryl
In preferred aspects, the invention further comprises a compound of formula 2:

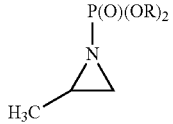
2 wherein the alkyl group is selected from the group consisting of methyl, ethyl or isopropyl.
In preferred aspects, the invention further comprises a compound of formula 2:

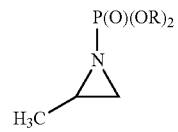
2 wherein the aryl group is phenyl.
In yet another preferred embodiment, there is provided a process for the synthesis of amphetamine derivatives comprising the step of performing an organo cuprate addition reaction upon an aziridine phosphoramidate compound to obtain an aryl or aryl-alkyl phosphoramidate amphetamine precursor.

In yet another preferred embodiment, there is provided a process for crystallization of compounds 6a-d from a mixture of compounds 6a-d and 8a-d, comprising the step of performing a crystallization using a mixture of two or more solvents wherein at least one of the two or more solvents is THF.

DETAILED DESCRIPTION OF THE INVENTION

Accordingly, the present invention relates to processes for the synthesis of amphetamine, dexamphetamine, methamphetamine, derivatives of these, including their salts, and novel precursors and intermediates obtained thereby, by synthesizing aziridine phosphoramidate compounds in specified solvents at specified temperatures, and then converting to a novel aryl or aryl-alkyl phosphoramidate precursor using an organometallic compound such as a copper salt, where the novel aryl or aryl-alkyl phosphoramidate precursor is then easily converted to the target compounds using known reactions, e.g. acid dephosphorylation, alkylation of the nitrogen followed by acid dephosphorylation, etc.

Alkyl means any C1-C10 straight or branched chain alkyl, wherein said alkyl, is optionally substituted with C1-C6 alkyl, C2-C6 alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, or sulfonyl.

Aryl means any alicyclic or aromatic, mono-, bi- or tricyclic, carbo- or heterocyclic ring, wherein the ring is either unsubstituted or substituted with one or more substituent(s) independently selected from the group including, but not limited to, alkylamino, amido, amino, aminoalkyl, azo, benzyloxy, C1-C9 straight or branched chain alkyl, C1-C9 alkoxy, C2-C9 alkenyloxy, C2-C9 straight or branched chain alkenyl, C3-C8 cycloalkyl, C5-C7 cycloalkenyl, carbonyl, carboxy, cyano, diazo, ester, formanilido, halo, haloalkyl, hydroxy, imino, isocyano, isonitrilo, nitrilo, nitro, nitroso, phenoxy, sulfhydryl, sulfonylsulfoxy, thio, thioalkyl, thiocarbonyl, thiocyano, thioester, thioformamido, trifluoromethyl, and carboxylic and heterocyclic moieties, including alicyclic and aromatic structures; wherein the individual ring size is 5-8 members; wherein said heterocyclic ring contains 1-6 heteroatom(s) independently selected from the group consisting of O, N, and S; and wherein said aromatic or tertiary alkyl amine is optionally oxidized. Useful carbo- and heterocyclic rings include without limitation phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

R may also be in certain preferred embodiments any C2-C10 straight or branched chain alkenyl or C1-C10 alkoxy, unsubstituted or optionally substituted with moieties listed above.

Copper includes CuCl, $CuCl_2$, CuBr, CuF, CuI, $Cu(OAc)_2$, Cu(OMe)2, Copper nanoparticles, Copper turnings, or combinations thereof. Copper nanoparticles means particles having an average diameter of about 1 nm-100 nm.

Alkyl Phosphonic Acid Protecting group means any group attached to the aziridine nitrogen having one or more alkyl groups attached to a phosphorous atom thereby having the formula P—O—(OR)$_2$, where R1 and R2 can be the same or different, and include without limitation any alkyl, alkoxy or aryl group as defined herein, and including any and all equivalents thereof.

Solvents, as used and exemplified herein, are not intended to be limiting and may include without limitation solvents selected from Ligroine, Pentane, Hexane, Heptane, Octane, Cyclopentane, Cyclohexane, Cycloheptane, Cyclooctane, Dichloromethane, Chloroform, Carbon tetrachloride, 1,2-Dichloroethane, 1,1,2,2-Tetrachloroethane, Methylacetate, Ethylacetate, Propylacetate, Butylacetate, Dimethylformamide, Diethylformamide, Dimethylacetamide, Diethylacetamide, Diethylether, Diisopropylether,[20] methyl tert-Butyl ether, THF, Dioxane, Acetonitrile, Sulfolane, DMSO, HMPT, NMP or mixtures of these solvents. Preferred solvents are Dichloromethane, Chloroform, Ethyl acetate, Propyl acetate, Butyl acetate, Dimethylformamide, Diethylformamide, Dimethylacetamide, Diethylacetamide, Diisopropylether, methyl tert-Butyl ether, THF, Dioxane, Acetonitrile or mixtures of these. Especially preferred solvents are Dichloromethane, Chloroform, Ethyl acetate, Butyl acetate, Dimethylformamide, Dimethylacetamide, methyl tert-Butyl ether, THF, Dioxane, Acetonitrile or mixtures of these.

The term, regioselective or regioselectivity, means without limitation, by way of explanation, the preference of one direction of chemical bond making or breaking over all other possible directions. It can often apply to which of many possible positions a reagent will affect, such as which proton a strong base will abstract from an organic molecule, or where on a substituted benzene ring a further substituent will add. Because of the preference for the formation of one product over another, the reaction is selective. This reaction is regioselective because it selectively generates one constitutional isomer rather than the other. When a reaction is regioselective to the point that no other regioisomers are observed, the reaction is defined as being regiospecific.

The term, stereoselective or stereoselectivity, means without limitation, by way of explanation, the property of a chemical reaction in which a single reactant forms an unequal mixture of stereoisomers during the non-stereospecific creation of a new stereocenter or during the non-stereospecific transformation of a pre-existing one. The selectivity arises from differences in steric effects and electronic effects in the mechanistic pathways leading to the different products.

Zwierzak et al. teach in Tetrahedron 1997, 53, 4935-4946 that the product from the organocuprate addition to the 2-alkyl-N-(diethylphosphoryl)aziridines is always regiospecific, always occurring with nucleophilic attack at the less substituted carbon atom of the aziridine ring. Zwierzak continues the paragraph by explaining that diethyl N-sec-alkylphosphoramidate products could be easily isolated in pure state after quenching the organocuprate reaction mixture with aqueous ammonium chloride solution and no further purification is necessary before deprotection. It was discovered in attempting to implement the Zwierzak procedure, that this is not the case. In fact, irrespective of the esters on the phosphoramidate, the crude product (6a, b, c or d) is not of acceptable purity to proceed with. Further, it has also been discovered that, where the process generates 3-5% of 8 (a, b, c or d respectively) in the crude product, that it could not be readily removed after the deprotection or later in the synthetic sequence. It was also found that if you used a single solvent recrystallization of 6a, then you did not remove the corresponding 8a. As example, 6a readily crystallizes from hexane, heptane, isooctane or petroleum ether, but the residual 8a is still present It is required to leave a residue of the reaction solvent (THF) in the solvent mixture to separate the 6a from 8a. Interestingly, it has been discovered that a ratio of specific solvents yielded the most preferred embodiment. This ratio comprises about 7 part heptane and 1 part THF for 6a. The other versions of 6 (b, c or d) needed other recrystallization solvent mixtures, but the common item was that it was required to leave a residue of THF in the mixture.

Experimental Introduction:

Unless otherwise noted, reagents and solvents were used as received from commercial suppliers.

NMR Spectra:

Proton nuclear magnetic resonance spectra were obtained on a Bruker AV 300 or a Bruker AV 500 spectrometer at 300 MHz and 500 MHz, respectively. Spectra are given in ppm ($\delta$) and coupling constants, J, are reported in Hertz. Tetramethylsilane was used as an internal standard for proton spectra.

HPLC Analyses:

Analyses were obtained on a Varian Prostar 210 HPLC system using a Prevail C18 column (53×7 mm, Alltech) with PDA detection at 208-210 nm and solvent gradient program Method A.

Method A:

| Time (min) | Flow (mL/min) | % A | % B |
|---|---|---|---|
| 0.0 | 2.0 | 95.0 | 5.0 |
| 10.0 | 2.0 | 5.0 | 95.0 |
| 11.5 | 2.0 | 5.0 | 95.0 |
| 11.6 | 2.0 | 95.0 | 5.0 |
| 13.0 | 2.0 | 95.0 | 5.0 |

A = Water with 0.05% v/v Trifluoroacetic Acid
B = Acetonitrile with 0.05% v/v Trifluoroacetic Acid Method B Flow rate: 0.7 mL/min Run time: 35 min Temp: ambient Mobile phase: 90% water pH=1.5 (perchloric acid): 10% Methanol

GC (FID):

Analyses were obtained on a Varian CP 3800 GC using a Supleco (Cat #24048) SPB-5 30×0.320; 0.25 μm column.

Column temperature initial: 50° C.

Column temperature final: 275° C.

Ramp profile: 20.0 deg/min

Injector temperature: 250° C.

Detector temperature: 250° C.

Carrier Gas/flow rate: Helium, 2 mL/min

Example 1

Preparation of diethyl (2methylaziridin-1-yl)phosphonate (2a)

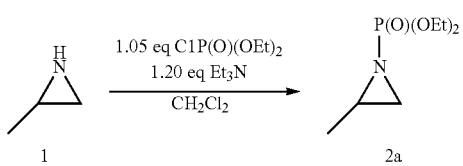

A 12 L 4-neck flask fitted with an overhead mechanical stirrer, temperature probe and 1 L pressure equalizing addition funnel was charged with 2-methylaziridine (300 g, 5.25 mol purchased from Menadiona SL of Barcelona, Spain), triethylamine (880 mL, 6.3 mol) and dichloromethane (3.0 L). The stirred solution was cooled to 5° C. and diethoxyphosphoryl chloride (804 mL, 5.51 mol) was added over 2.5 hours while maintain the internal temperature below 15° C. The reaction was then stirred for 18 hours, at which point the reaction was complete reaction was complete by TLC analysis (silica gel plate, 93:6:1 dichloromethane/MeOH/$NH_4OH$ and 6/3/1 $CHCl_3$/MeOH/$NH_4OH$; $KMnO_4$ stain). Water (3 L) was charged and the biphasic mixture was stirred for 20 minutes. The layers were separated and the organic layer was concentrated under reduced pressure. The remaining yellow oil was clarified by filtration. The filtrate (1028 g) was purified by short path vacuum distillation at 66-67° C., 1.0 mm Hg. to afford 2a as a colorless liquid (864.8 g, 85% yield, 99.0% GC purity). $^1$H NMR (300 MHz, $CDCl_3$) δ 4.15 (dq, J=8.0, 7.1 Hz, 4H), 2.64-2.45 (m, 1H), 2.33 (ddd, J=17.9, 5.9, 1.3 Hz, 1H), 1.91-1.81 (m, 1H), 1.34 (dt, J=7.1, 0.9 Hz, 6H), 1.28 (dd, J=5.4, 1.4 Hz, 3H).

Example 2

Preparation of diphenyl (2methylaziridin-1-yl)phosphonate (2b)

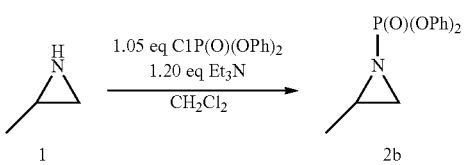

Compound 2b is prepared as described in Stephens, Moffett, Vaughan, Hill and Brown in the *Journal of Chemical and Engineering Data*, 1969, 14, 114-116, but substituting toluene for benzene, and is obtained as a thick colorless oil in about 55% yield after vacuum distillation. Expected $^1$H NMR (300 MHz, $CDCl_3$) δ 7.40-7.15 (m, 10H), 2.81-2.69 (m, 1H), 2.62-2.49 (dd, J=17.6, 5.6 Hz, 1H), 2.10-2.00 (dd, J=14.1, 4.9 Hz, 1H) and 1.28-1.24 ppm (m, 3H).

Example 3

Preparation of dimethyl (2methylaziridin-1-yl)phosphonate (2c)

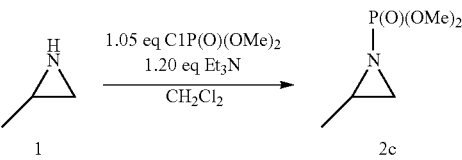

Compound 2c is prepared following the general procedure in Stephens, Moffett, Vaughan, Hill and Brown in the *Journal of Chemical and Engineering Data*, 1969, 14, 114-116 but substituting toluene for benzene, and is obtained as a colorless oil in about 73% yield after vacuum distillation (75-80° C. @ 10 mm Hg vacuum). Expected $^1$H NMR (300 MHz, $CDCl_3$) δ 3.80 (s, 3H), 3.76 (s, 3H), 2.65-2.50 (m, 1H), 2.42-2.31 (dd, J=17.6, 5.6 Hz, 1H), 1.92-1.85 (dd, J=14.1, 4.9 Hz, 1H), 1.28 (dd, J=5.4, 1.2 Hz, 3H).

Example 4

Preparation of diisopropyl (2methylaziridin-1-yl)phosphonate (2d)

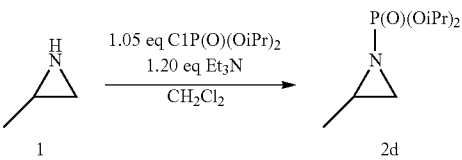

Compound 2d is prepared following the general procedure in Stephens, Moffett, Vaughan, Hill and Brown in the *Journal of Chemical and Engineering Data*, 1969, 14, 114-116 but substituting toluene for benzene, and is obtained as a colorless oil in about 80% yield after vacuum distillation (79-82° C. @ 3 mm Hg vacuum). Expected $^1$H NMR (300 MHz, $CDCl_3$) δ 4.71 (m, 2H), 2.64-2.41 (m, 1H), 2.28 (dd, J=17.6, 5.6 Hz, 1H), 1.81 (dd, J=14.1, 4.9 Hz, 1H), 1.34 (m, 12H) and 1.22 (dd, J=5.6, 1.2 Hz, 3H).

Example 5

Preparation of diethyl (2methylaziridin-1-yl)phosphonate (2a), Alternate Route

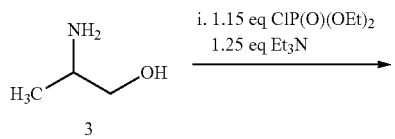

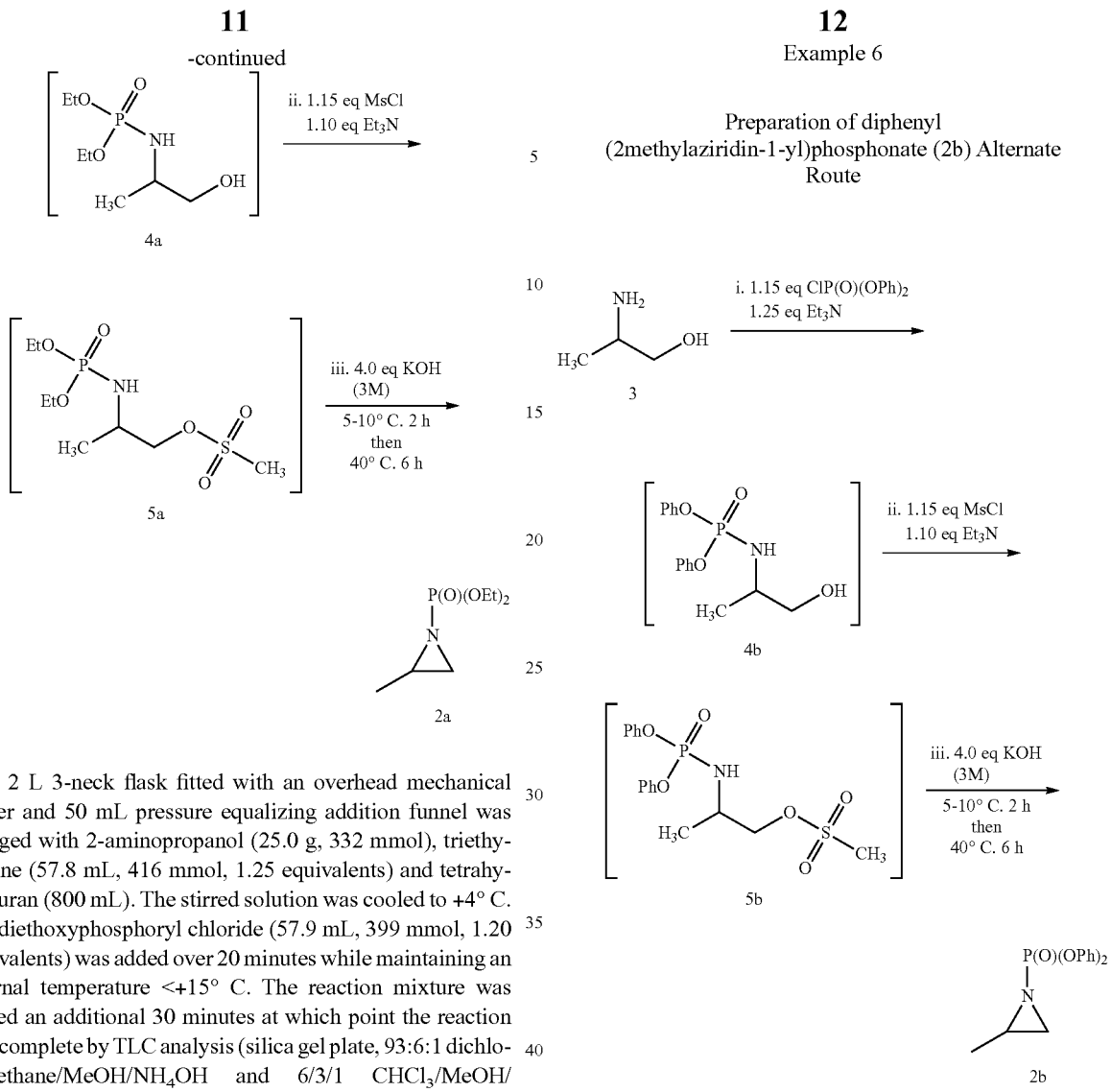

A 2 L 3-neck flask fitted with an overhead mechanical stirrer and 50 mL pressure equalizing addition funnel was charged with 2-aminopropanol (25.0 g, 332 mmol), triethylamine (57.8 mL, 416 mmol, 1.25 equivalents) and tetrahydrofuran (800 mL). The stirred solution was cooled to +4° C. and diethoxyphosphoryl chloride (57.9 mL, 399 mmol, 1.20 equivalents) was added over 20 minutes while maintaining an internal temperature <+15° C. The reaction mixture was stirred an additional 30 minutes at which point the reaction was complete by TLC analysis (silica gel plate, 93:6:1 dichloromethane/MeOH/NH$_4$OH and 6/3/1 CHCl$_3$/MeOH/NH$_4$OH; KMnO$_4$ stain). Additional triethylamine (57.8 mL, 416 mmol, 1.10 equivalents) was added to the reaction mixture and methanesulfonyl chloride (32.3 mL, 416 mmol, 1.25 equivalents) was added drop-wise over 25 minutes while maintaining an internal temperature <+18° C. The resulting reaction mixture was stirred for 1.5 hours at which time TLC analysis (see above methods) indicated the reaction was complete. Potassium hydroxide solution (3 M solution, 555 mL, 1.6 mol, 5.0 equivalents) was slowly added to the stirred reaction mixture while maintaining an internal temperature <+20° C. The reaction was stirred for 30 minutes and diluted with ethyl acetate (300 mL). The layers were separated and the aqueous layer was extracted with ethyl acetate (300 mL). The combined organic extract was washed with saturated sodium chloride solution (300 mL) and dried over anhydrous sodium sulfate. The solution was clarified and then concentrated under reduced pressure to afford crude 2 as an orange oil. The oil was purified by short path distillation (72-74° C., 10 mm Hg vacuum) to afford purified 2a as a colorless oil (48.2 g, 75% yield, 99.0% GC purity). $^1$H NMR (300 MHz, CDCl$_3$) δ 4.15 (dq, J=8.0, 7.1 Hz, 4H), 2.64-2.45 (m, 1H), 2.33 (ddd, J=17.9, 5.9, 1.3 Hz, 1H), 1.91-1.81 (m, 1H), 1.34 (dt, J=7.1, 0.9 Hz, 6H), 1.28 (dd, J=5.4, 1.4 Hz, 3H).

Example 6

Preparation of diphenyl (2methylaziridin-1-yl)phosphonate (2b) Alternate Route

Following the procedure for the alternate preparation of 2a, diphenyl (2methylaziridin-1-yl)phosphonate (2b) is prepared as a thick colorless oil in about 30% yield (expected minimum 97% GC purity). Expected $^1$H NMR (300 MHz, CDCl$_3$) δ 7.40-7.15 (m, 10H), 2.81-2.69 (m, 1H), 2.62-2.49 (dd, J=17.6, 5.6 Hz, 1H), 2.10-2.00 (dd, J=14.1, 4.9 Hz, 1H) and 1.28-1.24 ppm (m, 3H).

Example 7

Preparation of dimethyl (2methylaziridin-1-yl)phosphonate (2c) Alternate Route

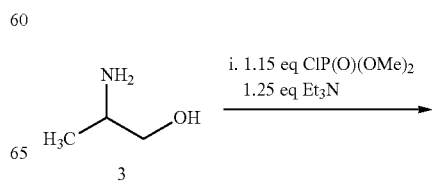

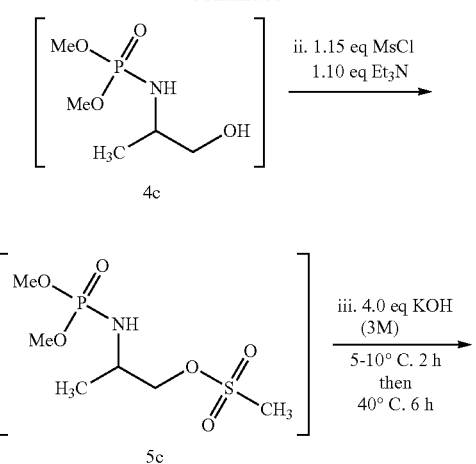

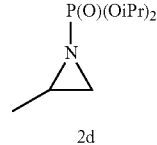

Following the procedure for the alternate preparation of 2a, dimethyl (2methylaziridin-1-yl)phosphonate (2c) is prepared as a viscous colorless oil in about 70% yield (expected 95% GC minimum purity). Expected ¹H NMR (300 MHz, CDCl₃) δ 3.80 (s, 3H), 3.76 (s, 3H), 2.65-2.50 (m, 1H), 2.42-2.31 (dd, J=17.6, 5.6 Hz, 1H), 1.92-1.85 (dd, J=14.1, 4.9 Hz, 1H), 1.28 (dd, J=5.4, 1.2 Hz, 3H).

Example 8

Preparation of diisopropyl (2methylaziridin-1-yl)phosphonate (2d) Alternate Route

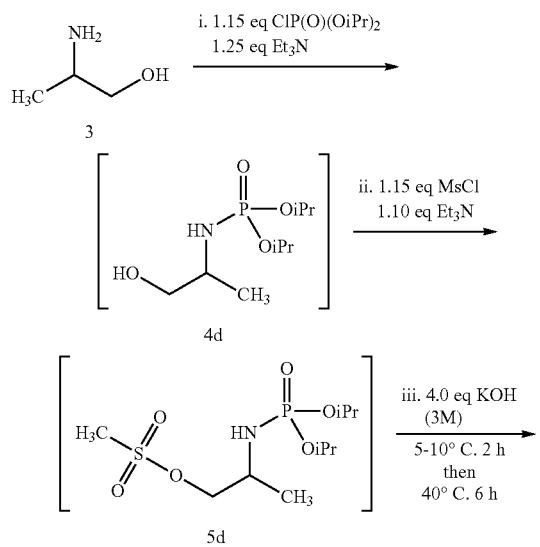

Following the procedure for the alternate preparation of 2a, diisopropyl (2methylaziridin-1-yl)phosphonate (2d) is prepared as a viscous colorless oil in about 50% yield (expected 95% GC minimum purity). Expected ¹H NMR (300 MHz, CDCl₃) δ 4.71 (m, 2H), 2.64-2.41 (m, 1H), 2.28 (ddd, J=17.6, 5.6, 1.3 Hz, 1H), 1.81 (dd, J=14.1, 4.9, 1.3 Hz, 1H), 1.34 (m, 12H) and 1.22 (dd, J=5.6, 1.2 Hz, 3H).

Example 9

Preparation of diethyl (1-phenylpropan-2-yl)phosphoramidate (6a) CuI catalyst

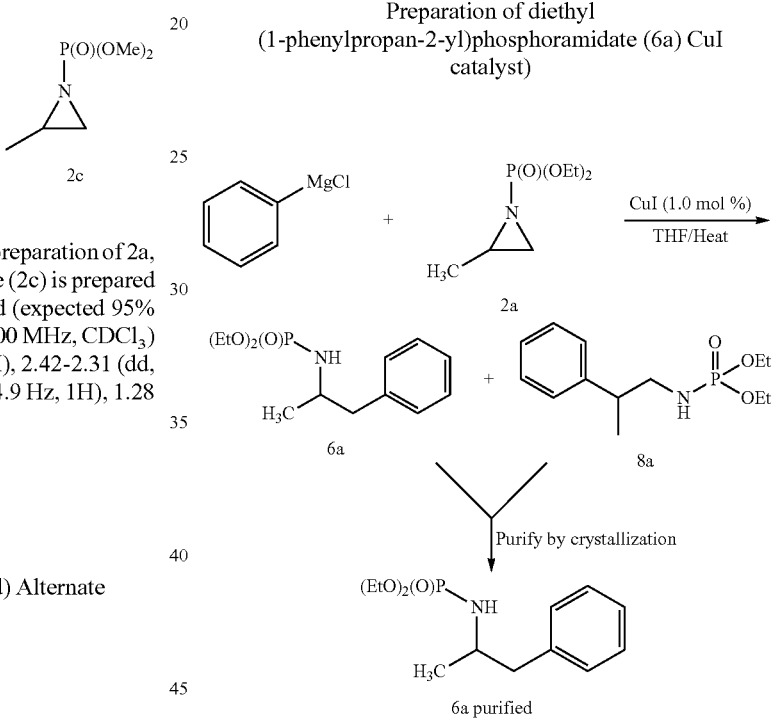

GC ratio = 97:3

A 250 mL, jacketed, three necked flask equipped with an overhead stirrer, 50 mL pressure equalizing addition funnel and a temperature probe was charged with 2a (10 g, 51.7 mmol), THF (50 mL) and CuI (98 mg, 1.0 mol %) and the stirred mixture was heated to 30° C. The pressure equalizing addition funnel was charged with PhMgCl (2M in THF, 32.36 mL) and the solution was added over 20 minutes while maintaining an internal temperature of 30-32° C. After the addition was complete, the reaction mixture was heated to 45-50° C. for an additional 30 minutes and then cooled to ambient temperature. The reaction was quenched by slow addition to a cooled mixture of saturated aqueous ammonium chloride solution and water (50/50 v/v, 100 mL) while maintaining an internal temperature below 20° C. The flask was rinsed with methyl t-butyl ether (100 mL) and the rinse was transferred to the quenched reaction mixture. The biphasic mixture was stirred for 5 minutes, allowed to separate for 20 minutes and then the aqueous phase was removed. The organic phase washed with saturated sodium chloride solution (50 mL) and the organic phase was dried over sodium sulfate. The solution (a 97:7 mixture of 6a: 8a by GC analysis) was filtered and concentrated under reduced pressure until the product began to crystallize. Heptane (40 mL) was added to the slurry and the mixture was heated until a solution was obtained. The stirred solution allowed to cool to room temperature and stirred for 18 hours. The solid was collected by filtration and dried under reduced pressure at 30° C. for 18 hours affording diethyl (1-phenylpropan-2-yl)phosphoramidate (6a) as a white crystalline solid (9.12 g, 65% yield; 99.72% GC purity with 0.04% 8a present). Mp 66-67° C. (lit[1] 57-58° C.). $^1$H NMR (300 MHz, CDCl$_3$) δ 7.36-7.08 (m, 5H), 4.14-3.85 (m, 3H), 3.85-3.66 (m, 1H), 3.58-3.32 (m, 1H), 2.81-2.61 (m, 2H), 2.38 (t, J=9.8 Hz, 1H), 1.38-1.18 (m, 6H), 1.15 (d, J=6.4 Hz, 3H).

Example 10

Preparation of diethyl (1-phenylpropan-2-yl)phosphoramidate (6a) [CuCl Catalyst]

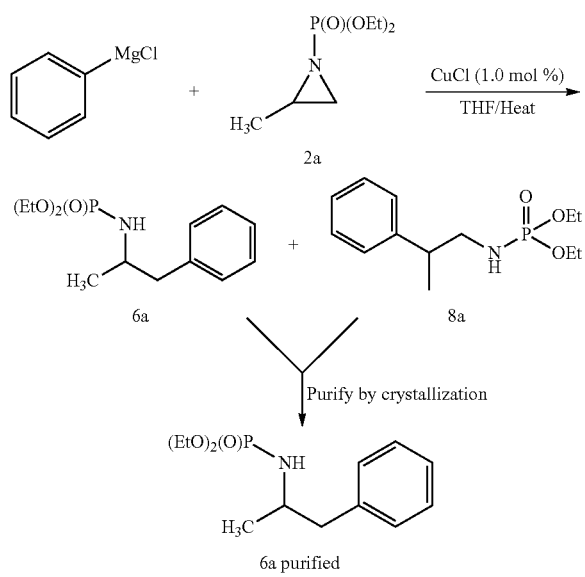

GC ratio = 97:3

A 12 L, jacketed, bottom outlet flask was charged with 2a (700 g, 3.62 mol), THF (3.5 L) and CuCl (3.58 g, 1.0 mol %) and the stirred mixture was heated to 45° C. A pressure equalizing addition funnel was charged with PhMgCl (2M in THF, 2.26 L) and the solution was added slowly while maintaining an internal temperature below 52° C. After the addition was complete, the reaction mixture was stirred at 48-51° C. for an additional 30 minutes. GC analysis indicated the consumption of 2a (<1.0%) and the reaction mixture was cooled to ambient temperature. The reaction was quenched by slow addition to a cooled mixture of saturated aqueous ammonium chloride solution and water (50/50 v/v, 4.2 L) while maintaining an internal temperature below 25° C. The flask was rinsed with heptanes (3.5 L) and the rinse was transferred to the quenched reaction mixture. The biphasic mixture was stirred for 5 minutes, allowed to separate for 20 minutes and then the aqueous phase was removed. The organic phase was concentrated under reduced pressure to a volume of about 1.0 L. The organic solution was azeotropically dried by two separate charges of heptanes (2×2.0 L) was added and the solution volume was adjusted by reduced pressure distillation to a total volume of about 2.5 L. The slurry was heated to 60-65° C. until the solids dissolved and then stirrer was slowed and the crystallization was allowed to proceed for about 24 hours as the batch cooled to ambient temperature. The slurry was cooled to 5° C. for about 1.5 hours. The resulting crystalline solid was collected by vacuum filtration and washed with cold heptanes (2×350 mL). After drying under vacuum at 35° C. for 48 hours the diethyl (1-phenylpropan-2-yl)phosphoramidate (6a) was obtained as a white crystalline solid (806.1 g, 82% yield; 99.90% GC purity with 0.04% 8a present). Mp 64-65° C. (lit[1] 57-58° C.). $^1$H NMR (300 MHz, CDCl$_3$) δ 7.36-7.08 (m, 5H), 4.14-3.85 (m, 3H), 3.85-3.66 (m, 1H), 3.58-3.32 (m, 1H), 2.81-2.61 (m, 2H), 2.38 (t, J=9.8 Hz, 1H), 1.38-1.18 (m, 6H), 1.15 (d, J=6.4 Hz, 3H).

The phenyl Grignard can be either be purchased commercial solutions, at about 2 moles of active reagent per liter of solution, or prepared in situ from the corresponding halobenzene and magnesium metal turnings. For phenylmagnesium chloride, the solvents of choice are either THF or 2-methylTHF. For phenylmagnesium bromide, the solvents of choice are either THF, 2-methylTHF or diethyl ether. For phenylmagnesium iodide the solvent of choice is diethyl ether. The use of any of these ether solvents (alone or mixed with toluene) in conversion to 2a to 6a, following the established procedure, affords 6a in comparable isolated yield, GC purity and devoid of the regioisomer 8a.

The use of other copper sources (CuCl$_2$, CuBr, CuF, Cu(OAc)$_2$, Cu(acac)$_2$, Cu(OMe)$_2$, Copper nanoparticles and Copper turnings) in conversion to 2a to 6a, following the established procedure, affords 6a in comparable isolated yield, GC purity and devoid of the regioisomer 8a.

Example 11

Preparation of diphenyl (1-phenylpropan-2-yl)phosphoramidate (6b)

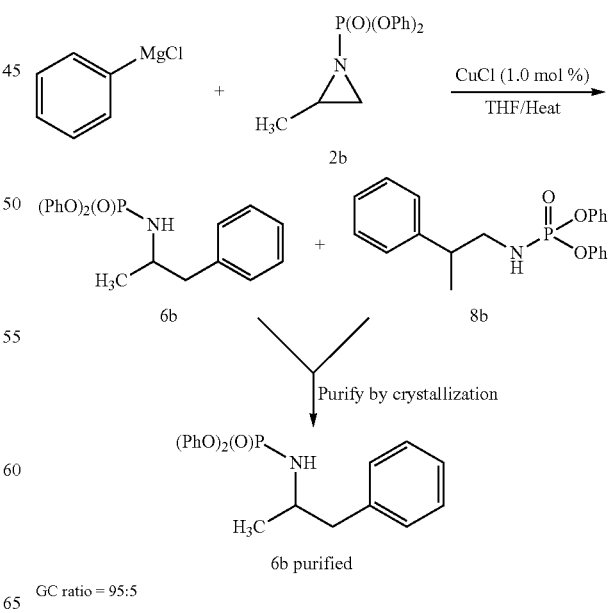

GC ratio = 95:5

A 100 mL, 3-necked flask equipped with an overhead stirrer, reflux condenser and pressure equalizing addition funnel was charged with 2b (10.0 g, 34.6 mmol), THF (50 mL) and CuCl (42 mg, 1 mol %) and the stirrer was started. The stirred mixture was heated to 48° C. and the pressure equalizing addition funnel was charged with PhMgCl (2M in THF, 17.4 mL). This solution was added slowly while maintaining a reaction temperature of 48-51° C. The reaction was allowed to stir at 48-51° C. for an additional 2 hours until the GC analysis indicated the consumption of 2b (<1.0%) and the reaction mixture was cooled to ambient temperature. The reaction was quenched by slow addition to a cooled solution of saturated aqueous ammonium chloride/water mixture (50/50 v/v, 60 mL) while maintaining the batch temperature below 20° C. Heptanes (60 mL) was used to rinse the reactor and was transferred to the quench mixture. The biphasic mixture was agitated for 15 minutes and the aqueous layer was removed. The organic layer washed with deionized water (20 mL) and the organic phase concentrated under reduced pressure to give viscous oil. This residue was dissolved in heptanes (50 mL) and the solution was concentrated under reduced pressure. The residue was crystallized from ethanol (1 g/5 mL) to give 6b as a white solid (9.05 g, 72% yield, 99.85% GC purity containing 0.05% of 8b). Mp 102-103° C. (lit[1] 101-102° C.). $^1$H NMR (300 MHz, CDCl$_3$) δ 7.38-7.11 (m, 15H), 3.83-3.65 (m, 1H), 3.00-2.89 (m, 1H), 2.86-2.78 (m, 1H), 2.73-2.62 (m, 1H), 1.15 (d, J=10.1 Hz, 3H).

Example 12

Preparation of dimethyl (1-phenylpropan-2-yl)phosphoramidate (6c)

mL). This solution was added slowly while maintaining an internal temperature of 48-51° C. The reaction was stirred at 48-51° C. for an additional 30 minutes until the GC analysis indicated the consumption of 2c (<1.0%) and the reaction mixture was cooled to ambient temperature. The reaction was quenched by slow addition to a cooled solution of saturated aqueous ammonium chloride in water (50/50 v/v, 100 mL) while maintaining the temperature below 20° C. Heptanes (100 mL) was used to rinse the reactor and the rinse solution was transferred to the quenched reaction mixture. The mixture was agitated for 15 minutes, allowed to separate for 30 minutes then the aqueous phase was discarded. The organic phase washed with deionized water (30 mL) and the organic phase concentrated under reduced pressure to give an oil. The residue was dissolved in heptanes (100 mL) and the solution was concentrated under reduced pressure. The residue was crystallized from methyl tert-butyl ether (1 g/3 mL), filtered and dried to give 6c as white needles (10.2 g; 74.8% yield), with 99.90% GC purity containing 0.06% 8c. Mp 86-88° C. $^1$H NMR (300 MHz, CDCl$_3$) δ 7.32-7.17 (m, 5H), 3.66 (d, J=6.4 Hz, 3H), 3.50-3.83 (m, 1H), 2.71 (d, J=6.6 Hz, 2H), 2.45 (m, 1H), 1.15 (d, J=6.6 Hz, 3H).

Example 13

Preparation of diisopropyl (1-phenylpropan-2-yl)phosphoramidate (6d)

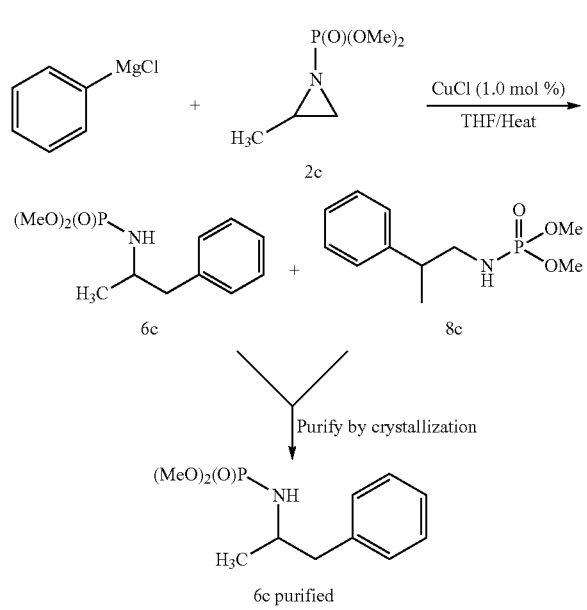

GC ratio = 97.5:2.5

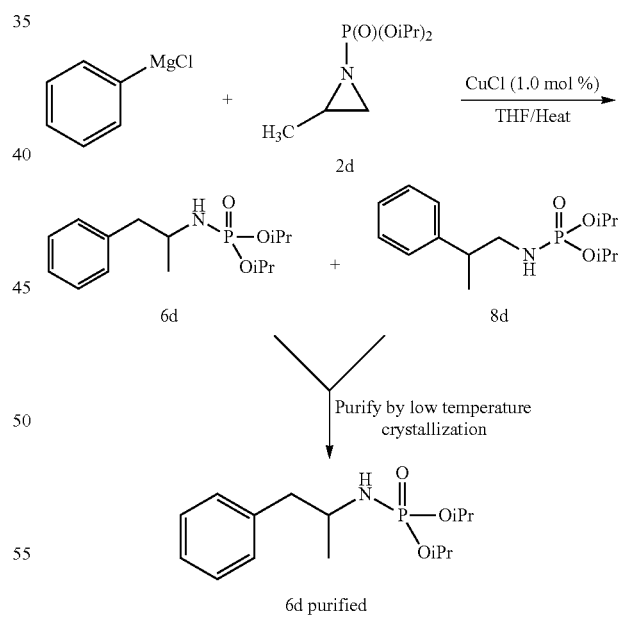

A 100 mL, 3-necked flask equipped with an overhead stirrer, reflux condenser and pressure equalizing addition funnel was charged with 2c (10.0 g, 60.5 mmol), THF (60 mL) and CuCl (70 mg, 1 mol %) and the stirrer was started. The mixture was heated to 48° C. and the pressure equalizing addition funnel was charged with PhMgCl (2M in THF, 13

Following the procedure for the alternate preparation of 6a, diisopropyl (1-phenylpropan-2-yl)phosphoramidate (6d) is prepared as a viscous colorless oil in about 50% yield (expected GC purity: >99.7% 6d with <0.1% 8d). Expected $^1$H NMR (300 MHz, CDCl$_3$) δ 7.32-7.17 (m, 5H), 4.59-4.41 (m, 2H), 3.53-3.41 (m, 1H), 2.86-2.80 (m, 1H), 2.69-2.61 (m, 1H), 2.36 (t, J=9.6 Hz, 1H), 1.32-1.26 (m, 12H), 1.08 (d, J=10.1 Hz, 3H).

Example 14

Preparation of amphetamine (7) from 6a

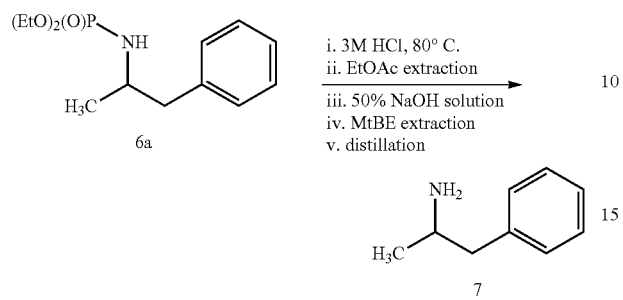

A 12 L, jacketed, bottom outlet valve flask was charged with 6a (800 g, 2.95 mol) and 3 M hydrochloric acid (3.0 L) and the reaction mixture was heated to 80° C. for 1.5 hours at which point HPLC analysis indicated that the reaction was complete, and then cooled to room temperature. The brown solution was washed with ethyl acetate (1.5 L) and the organic extract layer was discarded. Sodium hydroxide solution (50% solution, 560 mL) was slowly added to the remaining aqueous layer, keeping the temperature below 25° C. Methyl tert-butyl ether (1.0 L) was added and the mixture was agitated for 20 minutes then allowed to separate for 30 minutes. The aqueous layer was removed and the organic layer was concentrated under reduced pressure to afford a light yellow oil. This oil was short path distilled (75-78° C. at 10 mmHg vacuum) to give racemic amphetamine (7) as a clear colorless oil (335.76 g, 84.3% yield; 99.93% pure by GC). $^1$H NMR (300 MHz, CDCl$_3$) δ 7.36-7.26 (m, 2H), 7.23-7.13 (m, 3H), 3.26-3.03 (m, 1H), 2.72 (dd, J=13.2, 5.4 Hz, 1H), 2.53 (dd, J=13.2, 8.0 Hz, 1H), 1.20 (br s, 2H), 1.13 (d, J=6.3 Hz, 3H).

Example 15

Preparation of amphetamine (7) from 6b

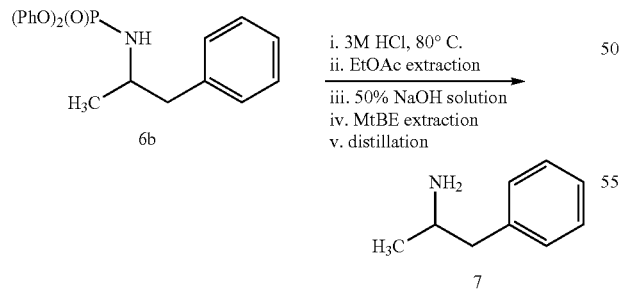

A 50 mL flask is charged with 6b (7.5 g, 20.41 mmol) and 3 M HCl (20.0 mL) and the stirred reaction mixture is heated to 80° C. for 32 hours, at which point HPLC analysis should indicate the reaction is complete, and it is cooled to room temperature. The organic layer is washed with ethyl acetate (2×25 mL) and the organic extracts are discarded. The aqueous layer is treated with sodium hydroxide solution (50%, 12.0 mL) keeping the temperature below 25° C. Methyl tert-butyl ether (50 mL) is added and the reaction mixture is agitated for 5 minutes and then separated. A second portion of methyl tert-butyl ether (50 mL) is added and the reaction mixture is agitated for 5 minutes. The combined organic extracts are washed with water (10 mL) and the organic layer is concentrated under reduced pressure to give 7 as a colorless oil in about 80% yield. The expected purity is >99% by GC purity and 99% by HPLC. The expected $^1$H NMR spectra (300 MHz, CDCl$_3$) is δ 7.36-7.26 (m, 2H), 7.23-7.13 (m, 3H), 3.26-3.03 (m, 1H), 2.72 (dd, J=13.2, 5.4 Hz, 1H), 2.53 (dd, J=13.2, 8.0 Hz, 1H), 1.20 (br s, 2H), 1.13 (d, J=6.3 Hz, 3H) and matches the reference spectra.

Example 16

Preparation of Amphetamine (7) from 6c

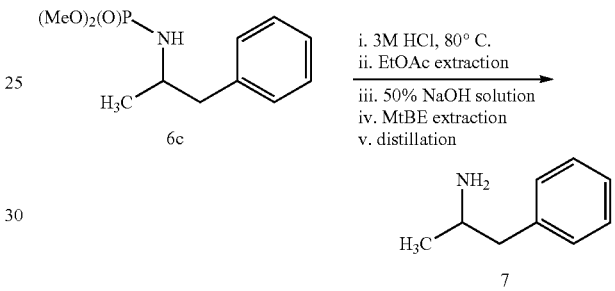

A 50 mL flask is charged with 6c (5.0 g, 20.6 mmol) and 3 M HCl (20.0 mL) and the stirred reaction mixture is heated to 80° C. for 1 hour, at which point HPLC analysis indicates the reaction is complete, and it is cooled to room temperature. The reaction mixture is washed with ethyl acetate (2×20 mL) and the organic extracts are disposed. The aqueous layer is treated with sodium hydroxide solution (50%, 12.0 mL) keeping the internal temperature below 25° C. Methyl tert-butyl ether (15 mL) is added and the reaction mixture is agitated for 15 minutes then allowed to separate. The organic layer is washed with water (10 mL) and organic layer is concentrated under reduced pressure to give 7 as a colorless oil in about 88.0% yield. The expected purity is >99.5% by GC and >99% by HPLC. The expected $^1$H NMR spectra (300 MHz, CDCl$_3$) is δ 7.36-7.26 (m, 2H), 7.23-7.13 (m, 3H), 3.26-3.03 (m, 1H), 2.72 (dd, J=13.2, 5.4 Hz, 1H), 2.53 (dd, J=13.2, 8.0 Hz, 1H), 1.20 (br s, 2H), 1.13 (d, J=6.3 Hz, 3H) and matches the reference spectra.

Example 17

Preparation of Amphetamine (7) from 6d

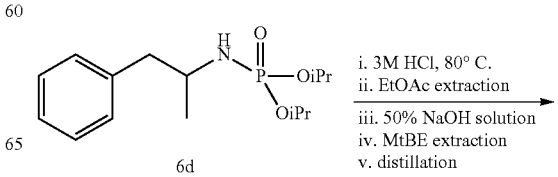

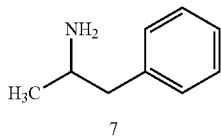

Following the procedure for the preparation of amphetamine (7) from 6a, amphetamine (7) is prepared from diisopropyl (1-phenylpropan-2-yl)phosphoramidate (6d) as a colorless oil. The expected $^1$H NMR spectra (300 MHz, CDCl$_3$) is δ 7.36-7.26 (m, 2H), 7.23-7.13 (m, 3H), 3.26-3.03 (m, 1H), 2.72 (dd, J=13.2, 5.4 Hz, 1H), 2.53 (dd, J=13.2, 8.0 Hz, 1H), 1.20 (br s, 2H), 1.13 (d, J=6.3 Hz, 3H) and matches the reference spectra.

Example 18

Preparation of Impurities 8a-d

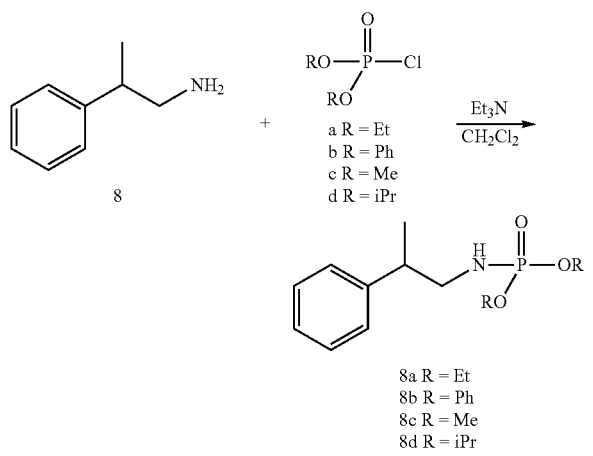

A 100 mL 3-neck flask was charged with commercial 8 (1.0 g, 7.4 mmol, from Aldrich Chemical), Et$_3$N (1.23 mL, 8.8 mmol), and dichloromethane (25 mL). The solution was cooled to 0-5° C. and a solution of the appropriate chlorophosphate (8.15 mmol of a through d) in dichloromethane (5 mL) was added over 5 minutes. The reaction mixture was allowed to stir at ambient temperature overnight. The reaction mixture was then quenched by adding water (20 mL) and the organic layer was separated. The organic extract was washed with 1N HCl solution (10 mL), saturated NaHCO$_3$ solution (10 mL), and saturated sodium chloride solution (10 mL). The organic phase was concentrated to dryness to afford the desired product, 8a-d.

8a: 81% yield, colorless oil. 95.8% GC purity. $^1$H NMR (300 MHz, CDCl$_3$) δ 7.30-7.19 (m, 5H), 3.68 (d, J=11.1 Hz, 3H), 3.63 (d, J=11.1 Hz, 3H), 3.20-3.00 (m, 2H), 2.95-2.80 (m, 1H), 2.45 (s, br, 1H), 1.26 (d, J=6.9 Hz, 3H).

8b: 91% yield, colorless oil. 95.16% GC purity. $^1$H NMR (300 MHz, CDCl$_3$) δ 7.26-7.04 (m, 15H), 3.48 (s, br, 1H), 3.35-3.22 (m, 1H), 3.03-2.90 (m, 2H), 1.21 (m, 3H).

8c: 85% yield, colorless oil. 97.47% GC purity $^1$H NMR (300 MHz, CDCl$_3$) δ 7.32-7.19 (m, 5H), 4.04-3.91 (m, 4H), 3.20-3.95 (m, 2H), 2.92-2.80 (m, 1H), 2.45 (s, br, 1H), 1.26 (d, J=6.9 Hz, 3H).

8d: The residue was chromatographed on a 40 g Combiflash Gold column eluting with 100% heptanes to 100% ethyl acetate over a 20-minute gradient. Combined clean fractions we concentrated to dryness to give the desired product as a clear colorless oil in 42% yield, 97.3% purity GC. $^1$H NMR (300 MHz, CDCl$_3$) δ 7.37-7.10 (m, 5H), 4.61-4.44 (m, 2H), 3.20-2.91 (m, 2H), 2.90-2.78 (m, 1H), 2.41-2.28 (m, 1H), 1.35-1.16 (m, 15H).

1) Cates, L. A.; Lawrence, W. H.; McClain, R. J. *Journal of Pharmaceutical Sciences*, 1966, 55, 1400-1403.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

What is claimed is:

1. A process of making a compound of Formula 6, said process comprising:
providing (Formula 2)

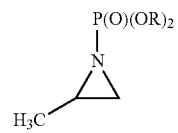

wherein R is alkyl or aryl and
reacting the compound of Formula 2 with phenylmagnesium halide and a copper catalyst under solvent and temperature conditions effective to produce
a compound of Formula 6

(Formula 6)

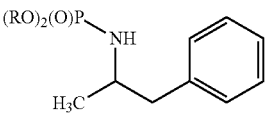

wherein R is alkyl or aryl; and,
purifying the compound of Formula 6 by crystallization using a mixture of two or more solvents, wherein one of the two or more solvents is residue THF;
wherein the Compound of Formula 6 has a regioisomeric purity >99%; and,
wherein the copper catalyst is CuCl, CuCl$_2$, CuBr, CuF, Cu(OAc)$_2$, Cu(acac)$_2$, Cu(OMe)$_2$, Copper nanoparticles, Copper turnings, or combinations thereof.

2. The process according to claim 1 wherein the copper catalyst is CuCl, CuCl$_2$, Copper nanoparticles, Copper turnings, or combinations thereof.

3. The process according to claim 1 wherein the copper catalyst is CuBr, CuF, Copper nanoparticles, Copper turnings, or combinations thereof.

4. The process according to claim 1 wherein the copper catalyst is Cu(OAc)$_2$, Cu(acac)$_2$, Cu(OMe)$_2$, Copper nanoparticles, Copper turnings, or combinations thereof.

5. The process according to claim 1, wherein the mixture of two or more solvents comprises a mixture of organic solvent and residual THF.

6. The process of claim 5, wherein the mixture of THF and heptanes is in a 7:1 ratio.

7. The process according to claim 1, wherein the mixture of two or more solvents is selected from: an organic ether-heptanes mixture: an organic ether-toluene mixture, an organic ether-heptanes-toluene mixture, an organic ether mixed with methyl-tert-butyl ether, wherein the organic ether is selected from the group consisting of diethyl ether, tetrahydrofuran, 2-methyltetrahydrofuran, and mixtures thereof.

8. The process according to claim 1, wherein the phenylmagnesium halide is either phenylmagnesium chloride, phenylmagnesium bromide or phenylmagnesium iodide.

9. The process according to claim 8 wherein the phenylmagnesium halide can either be commercially supplied or prepared in situ from the corresponding halobenzene and magnesium.

10. The process according to claim 9 wherein the magnesium can be in the form of chips, granules, ribbon, turnings, dust, grit, chunks, or combinations thereof.

11. The process according to claim 1, wherein said reacting the compound of Formula 2 with phenylmagnesium halide and a copper catalyst is carried out at a temperature of from 25° C. to 80° C.

12. The process according to claim 1, wherein said reacting the compound of Formula 2 with phenylmagnesium halide and a copper catalyst is carried out at a temperature of from 30° C. to 60° C.

13. The process according to claim 1, wherein the compound of Formula 6 contains less than 0.1% regioisomeric impurity.

14. The process according to claim 13, wherein the R=methyl, ethyl, isopropyl or phenyl.

15. The process according to claim 1, further comprising a step of deprotecting the compound of Formula 6 under acidic conditions effective to produce amphetamine of Formula 7

(Formula 7)

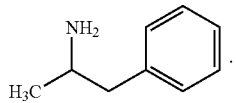

16. The process according to claim 15 wherein the acidic conditions are aqueous hydrochloric, sulfuric or phosphoric acids.

17. The process according to claim 16 wherein the aqueous acid water content is in an amount of 50% to 90%.

18. The process according to claim 15 wherein the R=methyl, ethyl, isopropyl or phenyl.

19. The process according to claim 1, wherein said providing a compound of Formula 2 comprises:
providing a compound of Formula 5

(Formula 5)

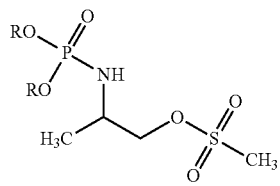

wherein R is alkyl or aryl; and
reacting the compound of Formula 5 with a base under conditions effective to produce a compound of Formula 2.

20. The process according to claim 19 wherein the R=methyl, ethyl, isopropyl or phenyl.

21. The process according to claim 19, wherein the base is potassium hydroxide or potassium carbonate.

22. The process according to claim 19, wherein said providing a compound of Formula 5 comprises:
providing a compound of Formula 4

(Formula 4)

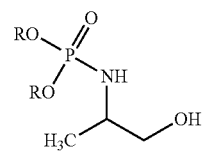

wherein R is alkyl or aryl; and
reacting the compound of Formula 4 with methanesulfonyl chloride and a base under conditions effective to produce a compound of Formula 5.

23. The process according to claim 22 wherein the R=methyl, ethyl, isopropyl or phenyl.

24. The process according to claim 22, wherein said providing a compound of Formula 4 comprises:
providing a compound of Formula 3

(Formula 3)

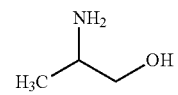

and
reacting the compound of Formula 3 with an appropriate

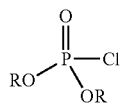

wherein R=alkyl or aryl
under conditions effective to produce a compound of Formula 4.

25. The process according to claim 24 wherein the R=methyl, ethyl, isopropyl or phenyl.

26. The process of claim 1, wherein the compound of the formula 6

(Formula 6)

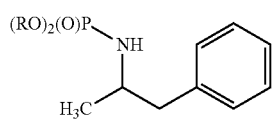

is produced in a regioisomeric purity of >1700:1
wherein: R is alkyl or aryl.

27. The process according to claim 26, wherein the alkyl group is selected from the group consisting of methyl, ethyl or isopropyl.

28. The process according to claim 26 wherein the aryl group is phenyl.
29. A process for the crystallization of compounds 6a-*d* from a mixture of compounds 6a-d and 8a-d, comprising the step of performing a crystallization using a mixture of two or more solvents wherein at least one of the two or more solvents is THF
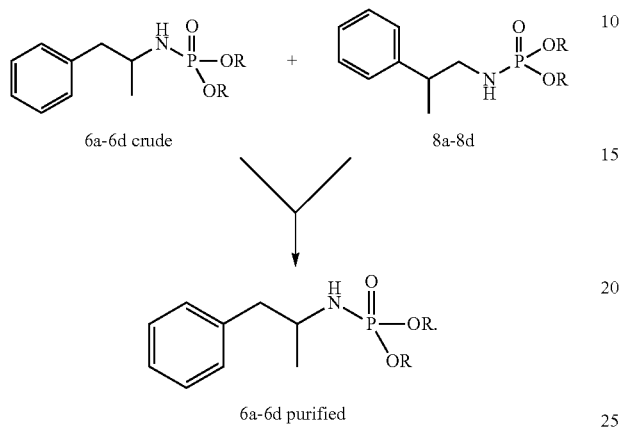
a. R = ethyl
b. R = phenyl
c. R = methyl
d. R = isopropyl
* * * * *